United States Patent [19]

Charles

[11] Patent Number: 5,018,513
[45] Date of Patent: May 28, 1991

[54] SHOULDER BRACE

[76] Inventor: Gene Charles, 8 Banyan Tree La., Irvine, Calif. 92715

[21] Appl. No.: 461,984

[22] Filed: Jan. 8, 1990

[51] Int. Cl.$^5$ .............................................. A61F 5/01
[52] U.S. Cl. .............................. 128/78; 128/DIG. 19; 2/44; 2/45
[58] Field of Search ............... 128/DIG. 19, DIG. 23, 128/77, 78, 85, 87; 2/44, 45; 450/2

[56] References Cited

U.S. PATENT DOCUMENTS

| | | |
|---|---|---|
| 3,277,889 | 5/1963 | Palmer .................... 128/DIG. 19 X |
| 3,499,441 | 3/1970 | Hall . |
| 3,906,944 | 9/1975 | Christen . |
| 4,198,964 | 4/1980 | Honneffer ........................ 128/87 R |
| 4,436,088 | 3/1984 | Finnieston . |
| 4,446,858 | 5/1984 | Verter . |
| 4,610,244 | 9/1986 | Hammond . |
| 4,628,913 | 12/1986 | Lerman .................................. 128/78 |
| 4,644,939 | 2/1987 | Coleman . |
| 4,735,198 | 4/1988 | Sawa . |
| 4,751,923 | 6/1988 | Marino . |
| 4,784,128 | 11/1988 | Scheuermann . |
| 4,785,803 | 11/1988 | Benckhuijsen . |
| 4,807,607 | 2/1989 | Roder . |
| 4,896,660 | 1/1990 | Scott ..................................... 128/77 |

OTHER PUBLICATIONS

Hohmann, G. *Pressure Pad Brace* (1941); FIG. 493.

Primary Examiner—Richard J. Apley
Assistant Examiner—L. Thomas
Attorney, Agent, or Firm—Stetina and Brunda

[57] ABSTRACT

A shoulder brace appliance comprising a pressure exerting element positionable about the human shoulder to exert at least anteroposterior pressure, and preferably both inferior and anteroposterior pressure, on the superior aspect of the shoulder. One or more positionig elements may be positionable on the patients body, (e.g. around the thorax) and attachable to the pressure exerting element to hold the pressure exerting element in a desired position on the patients shoulder. In a preferred embodiment, the pressure exerting element comprises first and second curved members attached at their top ends by way of a hinge. The hinges is positionable over top of the human shoulder such that the first curved member extends downwardly over the anterior shoulder and the second curved member extends downwardly over the posterior shoulder. When the first and second members are compressed inwardly, toward one another, such closure of the hinge will exert the desired anteroposterior pressure on the superior aspect of the shoulder. The first and second members may then be attached to one another so as to maintain the desired degree of anteroposterior pressure on the superior shoulder.

11 Claims, 2 Drawing Sheets

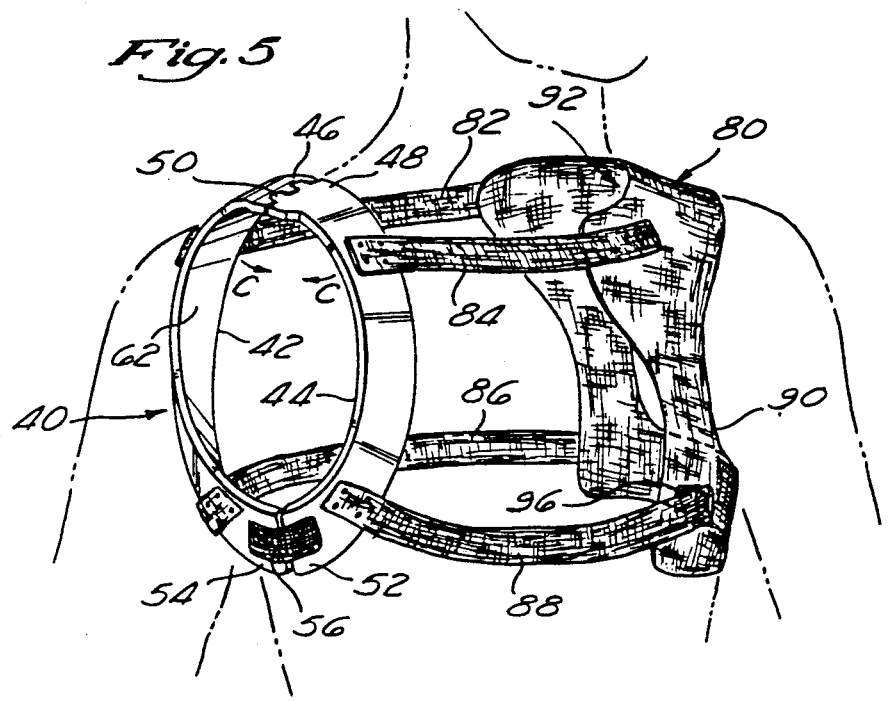
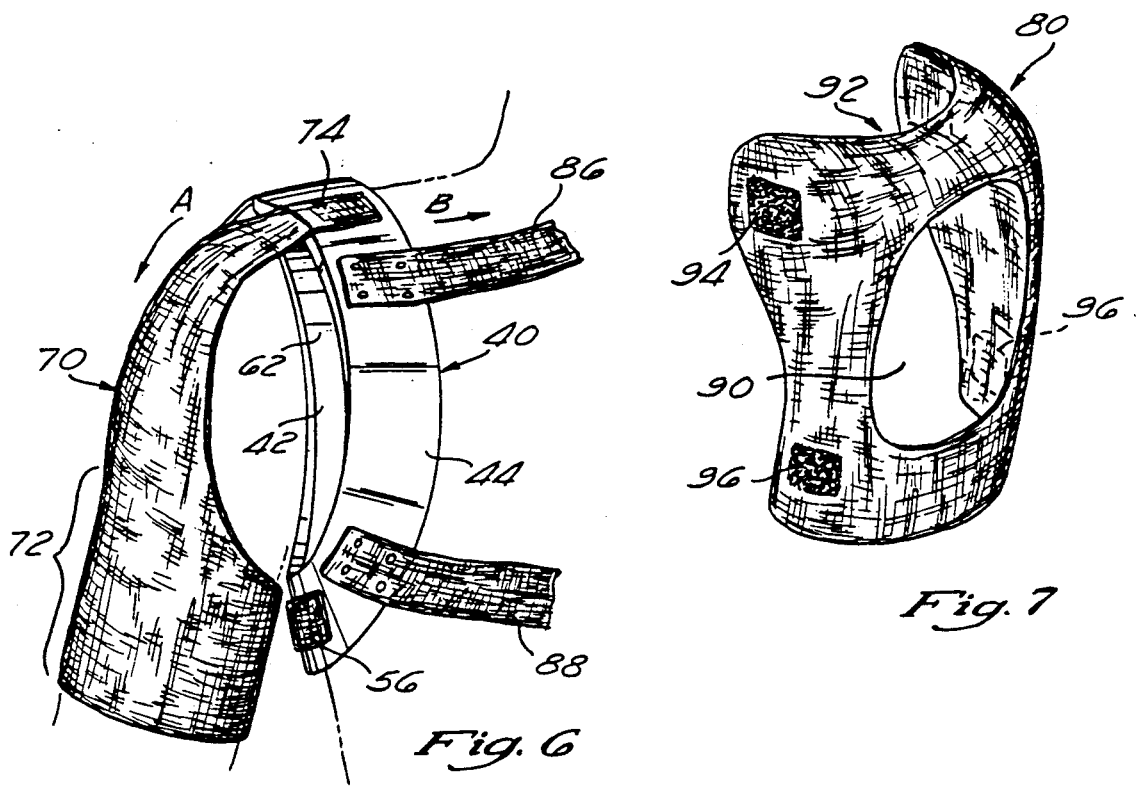

SHOULDER BRACE

FIELD OF THE INVENTION

This invention relates generally to the medical arts and more particularly to an appliance for treating dislocations, separations and other injuries of the acromioclavicular joint and/or superior aspect of the human shoulder.

BACKGROUND OF THE INVENTION

The superior aspect of the human shoulder is formed, in part, by the articulation of the lateral end of the clavicle with the acromion process of the scapula, forming the acromioclavicular joint--one of four joints which comprise the human shoulder The articular surfaces of the acromion process and the clavicle generally oppose one another with a cartilaginous articular disk sometimes being formed therebetween. Such articular disk, if present, partly and/or completely subdivides the space existing between the articular surfaces of the acromion process and the clavicle. The acromioclavicular ligament extends between the acromion process and the distal end of the clavicle, providing ligamentous interconnection therebetween. Further ligamentous stabilization of the distal clavicle and/or acromioclavicular junction is provided by a) the coracoacromial ligament which extends between the acromion and the coracoid process of the scapula, and b) the coracoclavicular ligament which connects the distal portion of the clavicle to the coracoid process.

The coracoclavicular ligament consists of two parts, the conoid ligament and the trapezoid ligament. These two portions of the coracoclavicular ligament are independently situated so as to resist upward movement of the clavicle and/or downward movement of the scapula and also to maintain proper anteroposterior alignment of the clavicle and scapula.

Injury to the acromioclavicular joint may result in stretching or disruption of one or more of the abovedescribed ligaments which stabilize the joint. Additionally, separation or disalignment of the clavicle and acromion may result in damage to or rupture of the relatively weak, flexible synovial capsule which surrounds the acromioclavicular joint. Such injuries often result in disruption of the normal anatomical alignment and positioning of the distal end of the clavicle relative to the acromion process.

Surgical intervention may be indicated in cases of severe traumatic rupture or tearing of the ligaments which stabilize the acromioclavicular junction. However, less dramatic injuries, such as stretching of the ligaments with or without concomitant damage to the synovial capsule, may be treated by non-surgical techniques aimed at restoring and maintaining proper alignment of the distal end of the clavicle with the acromion so as to permit natural healing of the ligaments, synovial capsule and/or surrounding tissues.

Non-surgical techniques heretofore employed in the treatment of acromioclavicular injuries have included a) taping of the shoulder with or without concomitant use of an arm-supporting sling and/or b) the application of one or more shoulder brace appliances known in the prior art.

Examples of shoulder brace appliances known in the prior art include the disclosures of U.S. Pat. Nos. 4,751,923; 4,784,128; 4,735,198; 4,785,803; 4,610,244; 3,906,944; 4,436,088; 4,644,939; 4,807,607; 4,446,858; 4,198,964 and 3,499,441.

Of particular note, the U.S. Pat. No. 4,198,964 (HONNEFFER) discloses a brace which is purportedly intended for treatment of acromioclavicular injuries. The HONNEFFER brace comprises a force-focusing member or shoulder pad positionable superior to the distal clavicle and attachable, by way of straps, to a) an arm sling and b) a body swathe or bandage member. The body swathe or bandage member fully wraps around the thorax and the upper portion of the involved arm. Thus, like many shoulder braces of the prior art, the HONNEFFER brace of U.S. Pat. No. 4,198,964 substantially immobilizes and impairs ROUTINE use of the involved arm. Furthermore, while some of the shoulder braces of the prior art may function to exert inferiorly directed pressure on the clavicle to correct superior displacement of the clavicle, none of these prior art braces are operative to exert anteroposterior pressure on the clavicle and/or acromioclavicular joint to correct anterior or posterior disalignment of the distal clavicle relative to the acromion.

In view of the shortcomings of the prior art there exists a need for an improved acromioclavicular brace or appliance capable of restoring and maintaining proper anatomical alignment of the acromioclavicular joint, including proper anteroposterior alignment thereof, while causing only minimal immobilization of the involved arm.

SUMMARY OF THE INVENTION

The present invention overcomes some or all of the shortcomings of the prior art through the provision of a shoulder brace appliance for the treatment of injuries to the acromioclavicular joint and/or other anatomical structures of the superior aspect of the human shoulder.

The shoulder brace appliance of the present invention comprises a pressure exerting element positionable about the human shoulder to exert at least anteroposterior pressure, and preferably both inferior and anteroposterior pressure, on the superior aspect of the shoulder. Additionally, one or more positioning element(s) may be positionable about a portion of the patient's body (e.g. around the thorax) and attachable to the pressure exerting element to hold the pressure exerting elements in a desired position on the patients shoulder.

The pressure exerting element may comprise a first curved or arcuate member and a second curved or arcuate member, pivotally interconnected at their top ends by way of a hinge or other pivotal connector. When positioned with the hinge over top of the human shoulder, the first curved or arcuate member extends downwardly over the anterior aspect of shoulder and the second curved or arcuate member extends downwardly over the posterior aspect of the shoulder. The bottom ends of the first and second curved or arcuate members thereafter, are, inwardly closeable or pivotal toward one another and connectable to one another, beneath the axilla. Upon inward closure of, or pivotal movement of, the first and second curved or arcuate members toward one another, the superior aspect of the shoulder will be captured between the first and second members such that the inner surfaces of the first and second members will exert anteroposterior pressure on the superior aspect of the shoulder. Such anteroposterior pressure may be employed to achieve therapeutic alignment of the acromioclavicular joint and/or proper positioning of the distal end of the clavicle.

In accordance with the further aspect of the invention, the shoulder brace appliance may further comprise an arm sleeve positionable about the upper arm of the involved shoulder and connectable to the top or other portion of the above-described pressure exerting element. When so connected, the arm sleeve will generally exert inferior and/or lateral pull on the upper portion of the pressure exerting element while causing corresponding upward lifting of the upper arm and/or some degree of abduction of the upper arm/shoulder. Such will serve to restore and/or insure proper inferior/superior alignment of the distal clavicle with the acromion.

In accordance with yet another aspect of the invention, the shoulder brace appliance may further comprise a contralateral shoulder yoke with attendant attachment straps. The shoulder yoke is positionable about the shoulder contralateral to the involved shoulder and the attendant straps are connectable to the pressure exerting element by way of any type of suitable connectors (e.g. VELCRO fastener material) to hold and stabilize the position of the pressure exerting element. In a preferred embodiment the contralateral shoulder yoke and attendant attachment straps will operate to pull the pressure exerting member in a medial direction, thereby offsetting or countervailing the laterally directed pull exerted by the above-described arm sleeve. By such arrangement, the concomitant laterally and medially directed forces exerted on the pressure exerting element will cooperate to hold the pressure exerting element in a desired position on the human shoulder (e.g. directly over the acromioclavicular joint). The forces exerted by the attachment straps may also cause inferiorly directed pull of the pressure exerting member to enhance the inferiorly directed pressure on the distal clavicle.

In accordance with a still further aspect of the invention, the various portions and/or elements of the shoulder brace appliance may be formed of any suitable materials. It is preferable that the pressure exerting element be formed of a generally rigid substance such as a molded plastic. The inner surfaces of the pressure exerting element may be provided with padding to enhance comfort to the wearer. Also, quantities of space occupying material may be deposited on specific regions of the inner surfaces of the first and second pressure exerting members to achieve a particular contour of the inner surface for purpose of customizing, localizing or contouring the therapeutic pressure exerted thereby. The remaining portions of the shoulder brace appliance, other than the pressure exerting element, are preferably formed of lightweight, air permeable materials to maximize comfort to the patient during use. It is preferable that the arm sleeve be provided with some elasticity to enhance its gripping of the upper arm.

Further aspects and advantageous of the invention will become apparent to those skilled in the art upon reading and understanding the following detailed description and consideration of the accompanying drawings.

BRIEF DESCRIPTION OF THE DRAWINGS

FIG. 5 is a perspective view of a preferred shoulder brace the present invention operatively disposed on the body of human being;

FIG. 6 is a cut-a-way perspective view of a portion of a preferred shoulder brace of the present invention operatively disposed on the shoulder of a human being and having the arm sleeve of FIG. 3 attached thereto and operatively positioned about the human beings arm;

FIG. 7 is a perspective view of a brace anchoring member positionable on the body of a human being and attachable to the preferred shoulder brace of the present invention so as to anchor and hold the shoulder brace in a desired position.

DETAILED DESCRIPTION OF A PREFERRED EMBODIMENT

The detailed description set forth below in connection with the appended drawings is intended as a description of the presently preferred embodiment of the invention, and is not intended to represent the only form in which the present invention may be constructed or utilized. The description sets forth the functions and sequence of steps of constructing and operating the invention in connection with the illustrated embodiments. It is understood, however, that the same or equivalent functions and sequences may be accomplished by different embodiments that are also intended to be encompassed within the spirit and scope of the invention.

Figure 1:
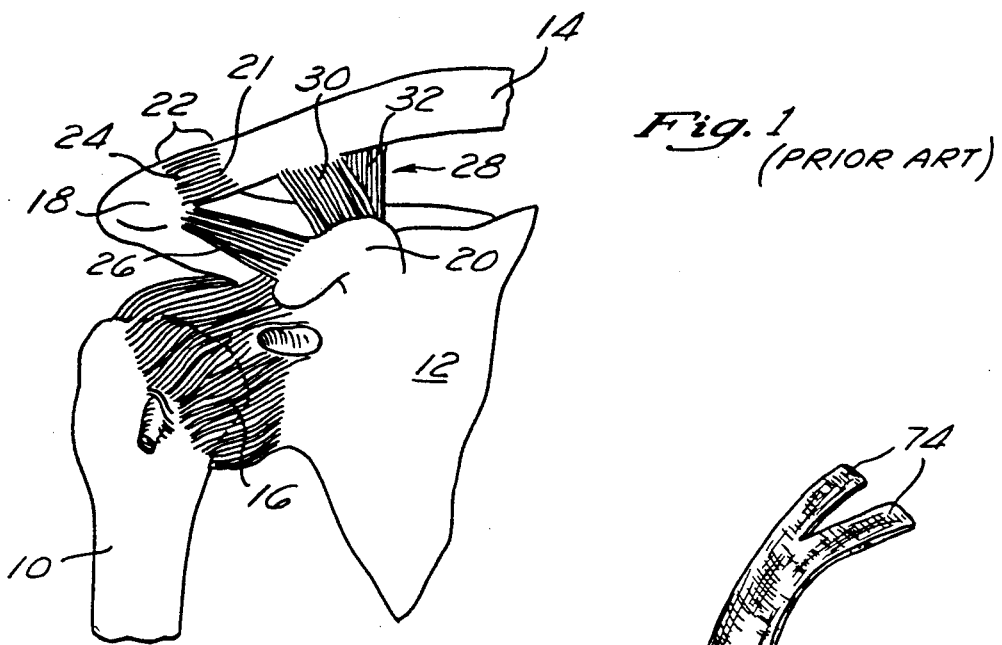
FIG. 1 is an illustration of a human shoulder joint.

The structure and function of the present invention can best be understood by first examining the anatomical configuration of the human shoulder. Thus, FIG. 1 provides an illustration of the bones and ligaments of the anterior aspect of the human shoulder. Referring to FIG. 1, the bones which form the human shoulder are the humerus 10, scapula 12 and clavicle 14. The head of the humerus (dotted lines) is a smooth rounded articular surface which partially inserts within and articulates with a socket or depression, known as the glenoid cavity, of the scapula 12. A fibrous synovial capsule 16 surrounds the articular head of the humerus 10 as it inserts within the glenoid cavity of the scapula 12.

The acromion is a projection which rises from the dorsal aspect of the scapula 12. Similarly, the coracoid process 21 projects upwardly from and bends anterolaterally relative to the superior border of the scapula 12, below the clavicle 14. The distal end 20, of the clavicle 14 articulates with the acromion 18 to form the acromioclavicular joint 22. A fibrous capsule 24 surrounds the acromioclavicular joint 22. An acromioclavicular ligament (not shown) underlines the capsule 24 and serves to connect the distal end 20 of the clavicle 14 to the acromion 18. A cartilaginous disk (also not shown) may exist between the distal end 20 of the clavicle 14 and the medial surface of the acromion 18 fully or partially subdividing the space existing therebetween. By such structure, the anatomy of the acromioclavicular joint 22 permits a limited degree of slidable movement of the clavicle 20 relative to the acromion 18.

Further stabilization and alignment of the acromion 18 and clavicle 14 are provided the coracoacromial ligament 26 which extends between the acromion 18 in the coracoid process 20 and the coracoclavicular ligament 28 which connects the clavicle 14 to the underlying coracoid process 20 of the scapula 12. The coracoclavicular ligament 28 actually consists of two parts, the trapezoid ligament 30 and the conoid ligament 32. The trapezoid 30 and conoid 32 ligaments cooperate to resist upward movement of the clavicle 14 or downward movement of the scapula 12. Additionally, the trapezoid 30 and conoid 32 ligaments serve to maintain proper anteroposterior alignment of the clavicle 14 such that the distal end 20 of the clavicle 14 will remain in proper articular relation to the acromion 18.

Traumatic injury to the shoulder may result in stretching or rupture of a) the acromioclavicular ligament (not shown) and/or b), the coracoacromio ligament 26 and/or, c) the trapezoid 30 and/or conoid 32 portions of the coracoclavicular ligament 28. In cases where one or more of these ligaments has been traumatically stretched or ruptured, the clavicle 14 may become displaced or misaligned relative to the acromion 18. Such displacement of the clavicle 14 may further result in damage to or rupture of the capsule 24 which surrounds the acromioclavicular joint 22. If one or more of the ligaments has been severely ruptured or torn, surgical intervention may be necessary. However, in the majority of cases involving stretching or strain of these ligaments non-surgical therapeutic intervention is the treatment of choice. In most cases, the aim of such treatment is to restore and maintain proper alignment of the clavicle 14 relative to the acromion 18 so that the joint capsule 24, acromioclavicular ligament (not shown), and/or coracoacromial ligament 26, and/or coracoclavicular ligament 28, as well as the surrounding tissues, may undergo a natural healing process.

Figure 3:
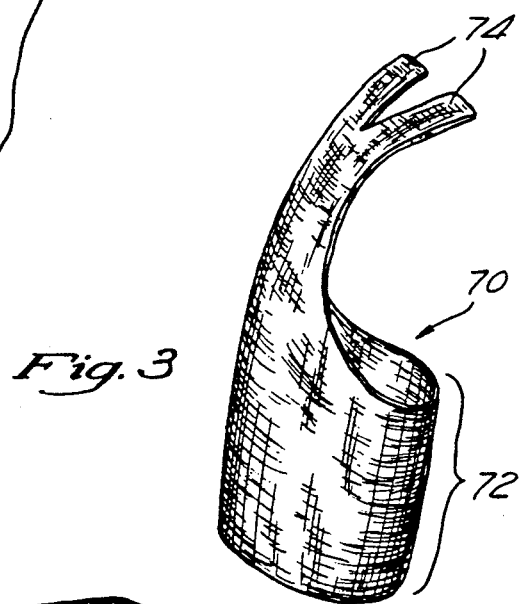
FIG. 3 is a perspective view of an arm sleeve which is attachable and may form a part of the shoulder brace shown in FIG. 2.
Figure 4:
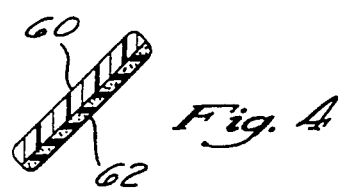
FIG. 4 is a cross-section through line 4—4 of FIG. 2.
Figure 2:
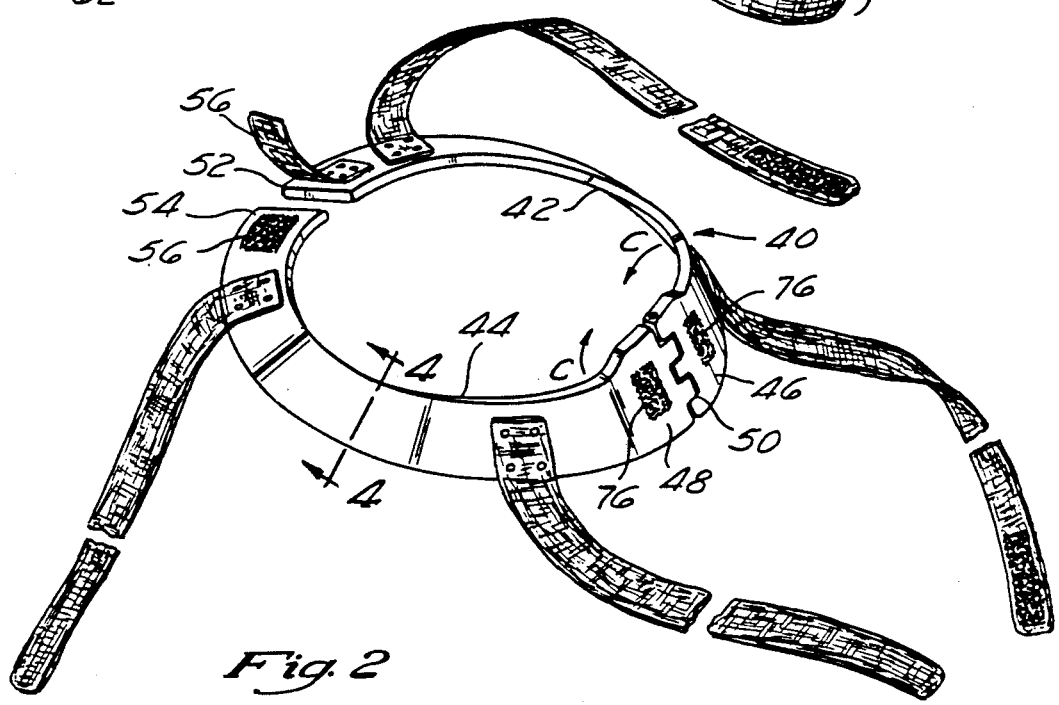
FIG. 2 is a perspective view of a preferred shoulder brace in accordance with the present invention.

In endeavoring to restore "proper" alignment of the acromioclavicular junction it is desirable, in at least some cases, to restore not only inferior-superior alignment of the clavicle with the acromion, but also to restore proper anterior-posterior alignment as well. The shoulder brace appliance of the present invention, as shown in FIG. 2, is employable for the purpose of restoring and maintaining such proper anterior-posterior alignment of the clavicle 14 and acromion 18. Additionally, the shoulder brace appliance of the present invention incorporates an arm sleeve (70 FIG. 3) which may be attached to the body of the shoulder brace appliance shown in FIG. 2 to exert downward or inferior pull on the brace appliance, and, corresponding upward or superior pull on the humerus 10.

A preferred shoulder brace appliance of the present invention shown in FIGS. 2-7 comprises a rigid or semirigid pressure exerting element 40 of an irregular ovoid configuration. The pressure exerting element 40 is formed of first 42 and second 44 generally curved or arcuate members, each forming one half of the pressure exerting element 40. The first 42 and second 44 members are pivotally joined at their top ends 46, 48 by way of a hinge 50. The bottom ends 52, 54 of the first and second members 44 and 42 are releasably connectable to one another by way of a connector 56 such as hook and loop material (e.g. VELCRO fastener material), or any other type of connector capable of holding the bottom ends 52, 54 of the curved members 42, 44 in fixed spacial relation and/or direct abutment with one another.

In this preferred embodiment, each curved member 42, 44 of the pressure exerting element 40 comprises a rigid plastic outer surface 60 with a cushioned inner surface 62. The cushioned inner surface 62 is formed of material such as fabric which is reasonably comfortable when placed in contact with the skin for extended periods of time. Additionally, the inner surface 62 may incorporate quantities of flexible plastic foam, padding, clay-like formable materials or other space occupying/pressure exerting matter, disposed in specific regions of each curved member 42, 44 such that, when the pressure exerting member 40 is operatively disposed on the shoulder of a human being, such space occupying/pressure exerting matter within the inner surface 62 of each curved member 42, 44 will function to exert desired therapeutic pressure on specific regions of the acromioclavicular joint 22 and surrounding structures. For example, the regions of the inner surface 62 of each curved member 42, 44, near the upper ends 46, 48 thereof, may be provided with quantities of padding, formable clay-like material, flexible foam, or other space occupYing material such that, when the pressure exerting element 40 is disposed on the shoulder of a human being in the manner shown in FIG. 5, such inner surface of the curved members 42, 44 will exert anteroposterior clamping pressure on or near the acromioclavicular joint 22 so as to hold the clavicle 14 and acromion 18 in proper anteroposterior alignment while, at the same time avoiding unnecessary traumatization or discomfort to the skin and underlying tissues of the anterior shoulder.

Also, it will be appreciated that the practitioner applying the shoulder brace appliance of the present invention may apply additional padding or other space occupying material to build up specific regions of the inner surfaces of the curved members 42, 44 to custom form such inner surfaces for the purpose of skewing or altering the pattern of pressure exerted by the pressure exerting element 40.

Additionally, all or part of the arcuate halves 42, 44 of the pressure exerting element 40 may be made of thermally formable or otherwise formable material so that the physician or other practitioner who is responsible for fitting and applying the appliance may custom form the curved members 42, 44 of the pressure exerting element 40 in such manner as to achieve a prescribed fit and prescribed therapeutic pressure on the affected acromioclavicular joint and/or other structures of the shoulder. Such will permit shoulder brace appliances of the present invention to be custom modified for patients of varying size, and body type and also to accommodate differing types of shoulder injuries which may be treatable with the device.

The attachable arm sleeve 70 is formed of flexible or semi-flexible material such as woven nylon, elastic, cotton or the like. It is preferable that the cylindrical bottom portion 72 of the arm sleeve fit snugly around the upper arm, in the region of the biceps. The bifurcated upper extension 74 of the arm sleeve 70 is attachable to connectors 76 formed on the upper ends 46, 48 of the curved members 42, 44, on either side of the hinge 50. The underside of the bifurcated upper extension and the connectors 76 may comprise hook and loop fastening material (e.g., VELCRO fasteners material) whereby the underside of the bifurcated upper extension may be easily attached to and/or detached from the pressure exerting element 40. When operatively connected to the pressure exerting element 40, as shown in FIG. 6, the arm sleeve 70 will exert lateral and inferiorly directed pulling pressure (arrow A) on the upper portion of the pressure exerting member 40 in the region of the acromioclavicular joint and will also serve to work a corresponding superior or upward lifting of the humerus 10.

To further anchor and hold the shoulder brace appliance to its operative disposition on the human shoulder, there is provided a contralateral shoulder yoke 80 with attendant connecting straps 82, 84, 86 and 88. The contralateral shoulder yoke 80 may be formed of any suitable material and is preferably formed of lightweight, loosely woven material such as cotton fabric, netting or the like so as to permit passage of air through to the underlying skin of the patient and to optimize patient comfort and compliance. Also, the contralateral shoulder yoke 80 may be made of disposable material so that, when soiled, it may be thrown away and replaced by another disposable yoke 80.

As shown in FIG. 5, the contralateral shoulder yoke 80 is positionable around the shoulder contralateral to the involved shoulder by passing the patients arm through the large armhole 90 formed in the yoke 80. A neck accommodating cut-away region 92 is formed in the upper portion of the yoke 80 such that, when disposed on the shoulder of the human patient, the neck accommodating region 92 will pass around the basal portion of the neck in a reasonable comfortable manner.

Straps 82, 84, 86 and 88 are connected to and extend between the pressure exerting member 40 and the contralateral shoulder yoke 80. The straps 82, 84, 86, 88 are permanently connected to the rigid pressure exerting member 40 by way of screws, rivets or other attachment members and are releasably connectable to the contralateral shoulder yoke 80 by way of any suitable type of releasable connector such as hook and loop type connectors (e.g. VELCRO fastener material) 94, 96.

OPERATION OF THE PREFERRED EMBODIMENT

After diagnosing an injury to the anterior shoulder and/or acromioclavicular joint 22, the practitioner will select a shoulder brace appliance of the present invention which is appropriately sized to fit the patient to be treated. The practitioner may thermally or otherwise form portions of the curved members 42, 44 of the pressure exerting member 40 in a preliminary fashion so as to emphasize or heighten the amount of pressure exerted in particular regions and/or to accommodate an anatomical variations in the size and structure of the patients shoulder. Additionally, the practitioner may opt to thermally form or add additional padding or other space occupying material to regions of the inner surface 62 of the pressure exerting element 40 so as to contour portions of the inner surface 62 in such manner as to exert specifically desired therapeutic pressure upon certain region(s) of the shoulder and/or acromioclavicular joint 22.

After preparation and/or the application of a desired padding or custom build-up material, the pressure exerting element 40 is placed over the shoulder of the patient such that the hinge 50 rests on superior aspect of the shoulder, just above the acromioclavicular joint 22 and/or distal portion of the clavicle 14. The bottom ends 52, 54 of the curved members 42, 44 are pulled together under the axilla of the involved arm and are joined by way of connector 56. Such pulling together at the bottom ends 52, 54 of the arcuate halves 42, 44 will cause the inner surfaces 62 of the curved members 42, 44 of the pressure exerting element to clamp or exert anteroposterior pressure on the superior aspect of the shoulder as indicated by arrow C. The arm sleeve 70 is then slidably pulled onto the upper portion of the involved arm and the upper extension 74 of the arm sleeve is attached to connecting members 76 formed on the outer surfaces of the top ends 46, 48 of the arcuate halves 42, 44, on either side of the hinge 50. When so positioned, the arm sleeve 70 will exert inferior and laterally directed pulling pressure on the upper portion of the pressure exerting element 40 as indicated by arrow A.

Thereafter, the contralateral shoulder yoke 80 is positioned on the patients shoulder contralateral to the involved shoulder by passing the uninvolved arm through the armhole 90 of the yoke 80. With the yoke 80 in its operative position on the contralateral shoulder, the straps 82, 84, 86 and 88 may be connected to connectors 94, 96 on the yoke 80. The straps will be precut or otherwise adjusted such that, when connected to the connectors 94, 96 on the yoke 80 they will pull transversely on the pressure exerting element 40 in the direction of arrow B. Such transverse pulling by the straps 82, 84, 86, 88 will generally countervail the lateral and inferiorly directed pressure (arrow A) pulling on the upper portion of the pressure exerting element 40 by the arm sleeve 70. Such countervailing forces (A and B) will cause the pressure exerting member 40 to remain in its proper lateral position over the acromioclavicular joint 22 of the involved shoulder. By maintaining such proper lateral positioning of the pressure exerting element 40 the clamping pressure (arrow C) exerted by the pressure exerting member 40 will maintain proper anteroposterior alignment of the distal clavicle 14 with the acromion 18. Additionally, the inferior and lateral pull (arrow A) of the arm sleeve 70 will have the effect of lifting the humerus 10 while exerting downward pressure on the clavicle 14, thereby helping to maintain superior/inferior positioning of the clavicle relative to the acromion 18 and preventing unnecessary pull on the injured joint by lifting and supporting at least some of the weight of the involved arm.

In some cases, it may be desirable to adjust the pressure exerting element 40 so that it resides over the distal aspect of the clavicle 14 somewhat medial to the acromion 18 such that the acromion itself will not be captured between the under surfaces 62 of the curved members 42, 44 of the pressure exerting element 40. This is a therapeutic decision to be reached by the practitioner at the time of application of the shoulder brace appliance. The desired positioning relative to the clavicle 14 and/or acromion 18 may be achieved by simply lengthening or shortening the strap 82, 84, 86, 88 and/or altering the position and/or size of the arm sleeve 70.

With the shoulder brace appliance operatively positioned on the body of the patient, the involved arm remains generally mobile and is not bound or held in a sling. In fact, the patient may be free to move the involved arm about with relative ease while the superior aspect of the shoulder remains substantially immobilized with alignment of the clavicle 14 and acromion 18 maintained by the various pressures exerted by the pressure exerting element 40.

Optimal efficacy of the shoulder brace appliance of the present invention may be achieved through substantially uninterrupted wearing of the shoulder brace appliance for a period of days or weeks. The appliance of the present invention may, however, be easily removed by the patient for brief periods while bathing and the like. This represents a distinct advantage over the prior art methods of shoulder taping whereupon, once the tape was cut away to permit bathing of the patient, it was generally necessary for the patient to revisit the practitioner in order to have the shoulder properly retaped following bathing. The shoulder brace of the present invention obviates the need for such repeat visits to the practitioner. Once it is properly fitted, the shoulder brace appliance of the present invention may be removed and redonned by the patient without requiring professional assistance.

Although the invention has been described herein with reference to a presently preferred embodiment, such is not intended to limit the scope of the invention in any way. Those skilled in the art will recognize various possible additions, modifications, deletions and alterations which may be applied to the above-described preferred embodiment of the invention. For example the first and second pressure exerting members need not necessarily be exact mirror images of one another and, in fact, may be size shaped and configured quite differently while still functioning to exert the above-described anteroposterior pressure on the superior shoulder. Additionally, various types of positioning members, other than the shoulder yoke and strap arrangement shown, may be employed. Indeed, it may be feasible to directly tape or otherwise affix the pressure exerting element to the desired portion of the shoulder, thereby eliminating the need for a separate positioning member or element such as the contralateral shoulder yoke shown in the drawings. It is intended that all such additions, modifications, deletions and alterations be included within the scope of the following claims and the equivalents thereof.

What is claimed is:

1. A shoulder brace comprising:
   a pressure exerting element positionable on the human shoulder to exert at least anteroposterior pressure on the superior aspect of the shoulder said pressure exerting element comprising:
   a first curved member having a top end and a bottom end;
   a second curved member having a top end and a bottom end;
   a hinge pivotally connecting the top end of the first curved member such that said hinge may be positioned on top of the shoulder with the first curved member extending over the anterior shoulder and the second curved member extending over the posterior shoulder;
   said first and second curved members being pivotal toward one another, about said hinge, so as to exert said anteroposterior pressure on said superior aspect of said shoulder;
   a connector for connecting the first curved member to the second curved member to prevent said first and second curved members from pivoting away from one another and maintain said anteroposterior pressure on the superior aspect to the shoulder; and
   a positioning element positionable on a portion of the body and attachable to said pressure exerting element in a substantially fixed position to hold said pressure exerting element on said shoulder.

2. The shoulder brace of claim 1 wherein:
   said positioning element comprises a contralateral shoulder yoke positionable about the shoulder contralateral to said pressure exerting element; and
   said connector comprises at least one connecting strap for connecting said contralateral shoulder yoke to said pressure exerting element to hold said pressure exerting element on said shoulder.

3. The shoulder brace of claim 1 further comprising:
   an arm sleeve positionable on the upper arm adjacent said shoulder and attachable to at least one point on said pressure exerting element.

4. The shoulder brace of claim 1 further comprising:
   an arm sleeve positionable on the upper arm adjacent said shoulder and attachable to the top end of at least one of said first and second curved members to exert at least laterally directed pull on said pressure exerting element.

5. The shoulder brace of claim 4 wherein the pressure exerting element and the arm sleeve are independently positioned and attached to the pressure exerting element such that the positioning element and the arm sleeve exert generally countervailing medially and laterally directed forces on the pressure exerting element so as to cooperatively hold the pressure exerting element in a substantially fixed position on the shoulder.

6. The shoulder brace of claim 1 wherein said pressure exerting element is formed of rigid plastic.

7. The shoulder brace of claim 1 wherein said pressure exerting element is formed of rigid material with flexible padding disposed on at least one surface thereof to provide comfort to the wearer of the brace.

8. The shoulder brace of claim 1 wherein at least a portion of said positioning element is made of formable material to permit a practitioner applying the brace to custom form said portion of the positioning element prior to application of the brace to the shoulder.

9. The shoulder brace of claim 1 wherein said first and second curved members are configurational mirror images of one another.

10. The shoulder brace of claim 1 wherein said pressure exerting element is sized and configured to exert both inferior and anteroposterior pressure on the superior shoulder.

11. The shoulder brace of claim 1 further comprising:
    an arm sleeve positionable on the arm adjacent said shoulder and attachable to the pressure exerting element so as to cause said pressure exerting element to exert inferiorly directed pressure on the superior aspect of the shoulder.

* * * * *

UNITED STATES PATENT AND TRADEMARK OFFICE
CERTIFICATE OF CORRECTION

PATENT NO. : 5,018,513
DATED     : May 28, 1991
INVENTOR(S) : Gene Charles

It is certified that error appears in the above-identified patent and that said Letters Patent is hereby corrected as shown below:

```
Column 1, line 16, after "shoulder" please add--.--
Column 1, lines 41-42, delete "abovedescribed" and insert
--above-described--
Column 4, line 36, please delete "!2" and insert therefor --12--
Column 4, line 44, please delete "!2" and insert therefor --12--
Column 5, line 24, please delete "!8" and insert therfor --18--
Column 5, line 39, please delete "(70 FIG. 3) and insert
    therefor "70 (FIG. 3)--
Column 6, line 12, please delete "occupYing" and insert
    therefor "occupying""
Column 6, line 15, after "surface" please add --62--
Column 6, line 54, please delete "fasteners" and insert
    therefor --fastener--
Column 6, line 66, please delete "to" and insert therfor --in--
Column 8, line 26, please delete "!8" and insert therfor --18--
Column 9, line 7, please delete "Will" and insert therefor --will--
```

Signed and Sealed this

Fifteenth Day of September, 1992

Attest:

DOUGLAS B. COMER

*Attesting Officer*   *Acting Commissioner of Patents and Trademarks*